US00PP16199P2

(12) United States Plant Patent
Tristram

(10) Patent No.: US PP16,199 P2
(45) Date of Patent: Jan. 10, 2006

(54) ***HELLEBORUS* PLANT NAMED 'WALHELIVOR'**

(50) Latin Name: ***Helleborus* hybrid**
Varietal Denomination: Walhelivor

(76) Inventor: David Tristram, Walberton Nursery, Yapton Lane, Walberton, Arundel (GB), BN18 OAS ( * ) Notice: Subject to any disclaimer, the term of this patent is extended or adjusted under 35 U.S.C. 154(b) by 109 days.

(21) Appl. No.: 10/836,139

(22) Filed: May 3, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—Louanne Krawczewicz Myers

(57) ABSTRACT

A new cultivar of *Helleborus* named 'Walhelivor' that is characterized by a tidy upright habit, ivory-white flowers, contrasting burgundy-pink buds, and medium green foliage. In combination these traits set 'Walhelivor' apart from all other existing varieties of *Helleborus* known to the inventor.

2 Drawing Sheets

Genus: *Helleborus.*
Species: hybrid.
Denomination: Walhelivor.

BACKGROUND OF THE INVENTION

The present invention relates to a new and distinct cultivar of *Helleborus* that is grown for use as an ornamental plant for the garden and landscape. The new cultivar is known botanically as *Helleborus* hybrid and will be referred to hereinafter by the cultivar name 'Walhelivor'.

'Walhelivor' resulted from a breeding program that was established by the inventor in 1980 in a cultivated area of Sussex, England. The purpose of the breeding program was to produce new *Helleborus* plants exhibiting vigorous growth rate, upright form, and flatness of flowers. 'Walhelivor' is a hybrid plant that was selected by the inventor in 1995 on the basis of a combination of commercially useful characteristics, including vigor, crop uniformity, plant habit and flatness of flowers.

Commencing in 1980, the inventor assembled and hybridized various *Helleborus* plants and *Helleborus* seed strains, including selected seedlings of *Helleborus niger* 'Potter's Wheel' strain, unpatented which the inventor regarded as having promising characteristics of vigor, form and presentation of flowers. Seedlings resulting from each year's hybridizations were grown to first year flowering, and a select number was retained for second year evaluation. By 1995, the inventor had extracted a collection of promising selections from which 'Walhelivor' was selected in that year as a single plant. The parents of 'Walhelivor' are unknown. 'Walhelivor' is derived from plants which have resulted from the hybridization of plants (seedlings) of *Helleborus niger, Helleborus×nigercors,* and *Helleborus×ericsmithii.*

'Walhelivor' is a perennial that exhibits vigorous growth, tidy upright habit, large ivory-white flowers, contrasting burgundy-pink buds, and medium-green leaves. The distinguishing characteristics that make 'Walhelivor' unique are crop uniformity, vigorous growth rate, tidy plant habit and well presented flat ivory-white flowers that gradually turn pink, then age to green.

The closest comparison plants in commerce, known to the inventor, are the various seed-raised unnamed plant selections which may be listed as, or listed as being from *Helleborus niger, Helleborus×nigercors,* or *Helleborus× ericsmithii.* 'Walhelivor' is distinguishable from such plants by its vigorous yet tidy habit, its large flowers borne prolifically and which are distinctly ivory-white in color when they open, are tinged pink when mature, and turn green, as they age.

The first asexual propagation was accomplished by the inventor in 1999 in a cultivated area of Sussex, England. Asexual propagation of the new cultivar 'Walhelivor' was conducted by the inventor using the method of tissue culture. The unique features of 'Walhelivor' proved stable and the plant reproduces true to type in successive generations of asexual propagation.

SUMMARY OF THE INVENTION

The following represent the distinguishing characteristics of the new *Helleborus* cultivar 'Walhelivor'. In combination these traits set 'Wahelivor' apart from all other existing varieties of *Helleborus* known to the inventor. 'Walhelivor' has not been tested under all possible conditions and phenotypic differences may be observed with variations in environmental, climatic, and cultural conditions, however, without any variance in genotype.

1. *Helleborus* 'Walhelivor' exhibits large flat ivory-white flowers, with green markings, that later turn pink, and age to green in color.
2. *Helleborus* 'Walhelivor' exhibits prolific flowering with six spikes of twelve flowers each, on a 1-gallon container plant at 2-years-of-age.
3. *Helleborus* 'Walhelivor' is readily propagated in vitro and readily rooted ex vitro.
4. *Helleborus* 'Walhelivor' produces a uniform crop.
5. *Helleborus* 'Walhelivor' exhibits a vigorous growth rate.
6. *Helleborus* 'Walhelivor' exhibits medium-green foliage.
7. *Helleborus* 'Walhelivor' is 46 cm. in height and 51 cm. in width at 2-years-of-age.
8. *Helleborus* 'Walhelivor' exhibits contrasting burgundy-pink flower buds.
9. *Helleborus* 'Walhelivor' is hardy in USDA Zones 4–5.

BRIEF DESCRIPTION OF THE DRAWINGS

The accompanying color drawings illustrate the overall appearance of the new *Helleborus* variety 'Walhelivor' showing the colors as true as it is reasonably possible to obtain in colored reproductions of this type. Colors in the drawings may differ from the color values cited in the detailed botanical description, which accurately describe the actual colors of the individual plant from which data was collected.

The drawing shown as FIG. 1 illustrates a two-year old plant from a side perspective.

Figure 1:
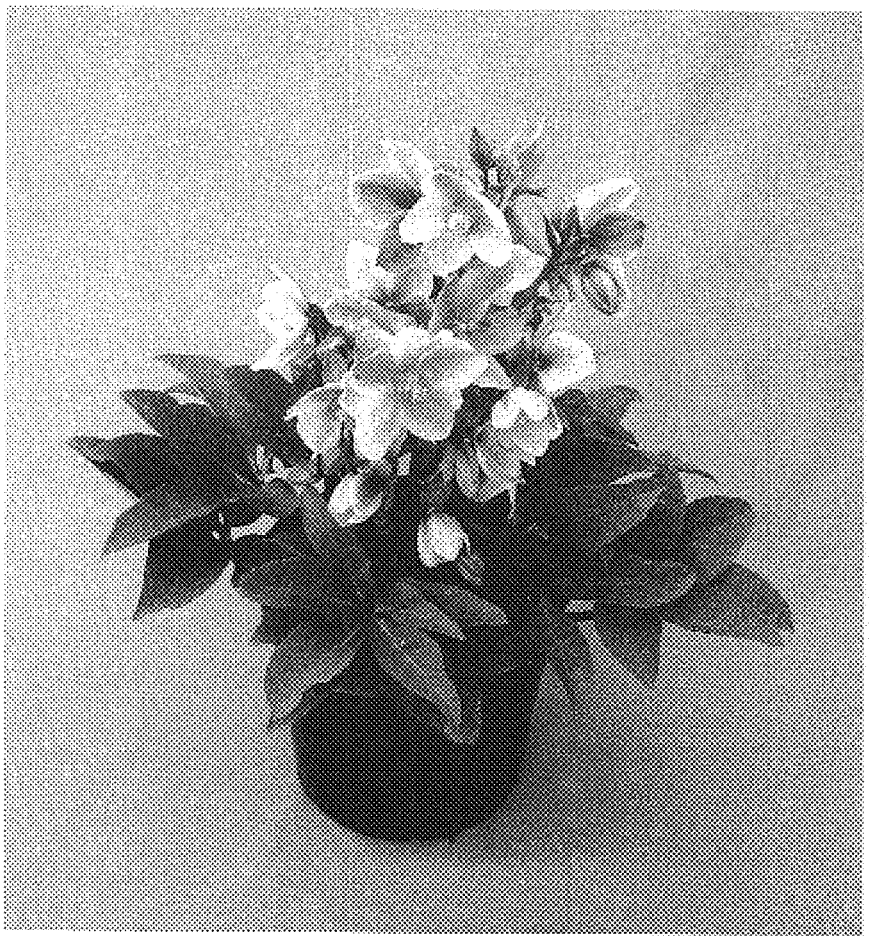
Figure 2:
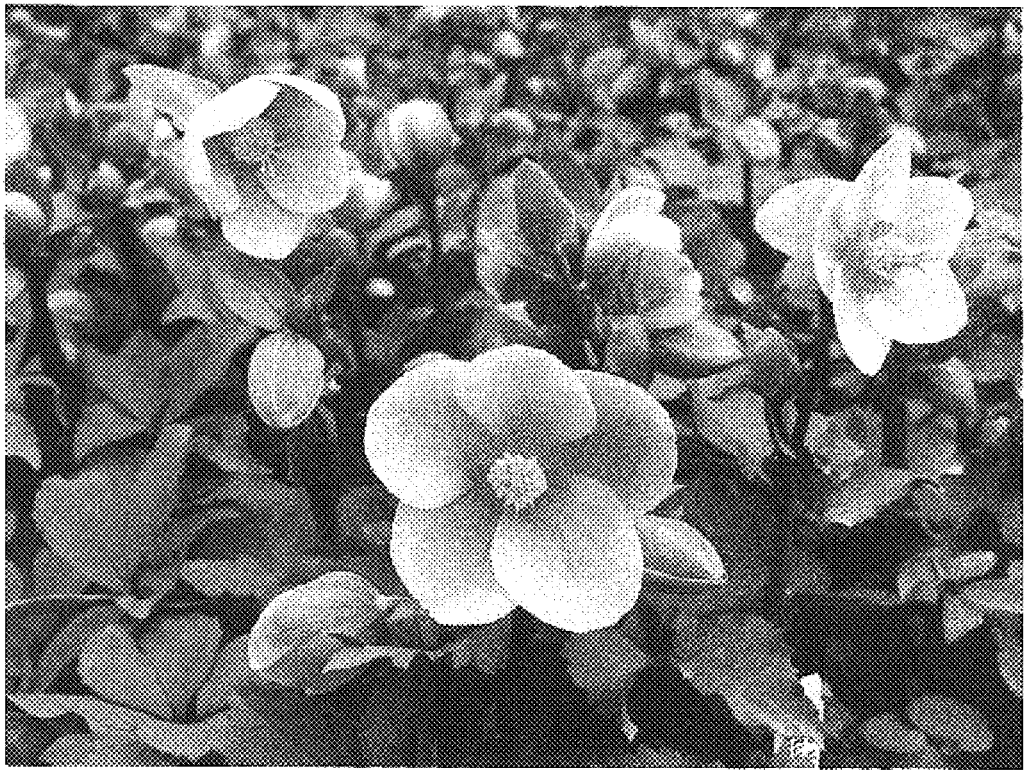

The drawing shown as FIG. 2 is a close-up view of buds and newly-opened flowers. All drawings are made using conventional techniques and although foliage colors may appear different from actual colors due to light reflectance, they are as accurate as possible by conventional photography.

BOTANICAL DESCRIPTION OF THE PLANT

The following is a detailed description of the *Helleborus* cultivar named 'Walhelivor'. Data was collected in Arroyo Grande, Calif. from 2-year-old plants grown in 2-gallon containers out-of-doors. Color determinations are in accordance with the 2001 Royal Horticultural Society Colour Chart except where general color terms of ordinary dictionary significance are used. The growing requirements are similar to the species.

Botanical classification: *Helleborus* 'Walhelivor'.
Species: hybrid.
Common name: Hellebore.
Use: Ornamental.
Parentage: 'Walhelivor' is derived from plants which have resulted from the hybridization of plants (seedlings) of *Helleborus niger, Helleborus×nigercors, Helleborus× ericsmithii.*
Commercial classification: Perennial.
Vigor: Highly vigorous.
Habit: Upright and compact.
Height (at 2 years): 46 cm. in height.
Width (at 2 years): 51 cm. in width.
Hardiness: USDA Zones 4–5.
Propagation: Micro-propagation.
Root system: Fibrous.
Soil: Plant in deep fertile soil that is rich with humus.
Sunlight: Plant in moderate to filtered shade. Performs best under deciduous trees.
Time to initiate rooting: 4–6 weeks are needed to produce roots.
Temperature to initiate rooting: Rooting is initiated at 18 degrees Centigrade air temperature.
Crop time: 6–8 months are needed to produce a finished 1-gallon container from a weaned micropropagule.
Seasonal interest: Ivory-white flowers and burgundy-pink buds in spring and summer.
Disease and pests: Susceptible to *Coniothyrium hellebori* and hellebore aphids.
Other: Living and dried plants are poisonous.
Stem:
- *Stem shape.*—Cylindrical.
- *Stem diameter.*—1.50 cm. in diameter.
- *Stem length.*—15 cm. in length.
- *Surface.*—Glabrous.
- *Lenticels.*—None present.
- *Stem color.*—Individual colors 187A and 191A are both present on stem.
- *Internode length.*—1 cm. between nodes.
- *Branching habit.*—Basal shoots.

Foliage:
- *Type.*—Evergreen.
- *Leaf arrangement.*—Pedate.
- *Leaf division.*—Compound.
- *Petiole shape.*—Elliptic in cross section.
- *Petiole color.*—187A.
- *Petiole surface.*—Glabrous and fluted.
- *Petiole texture.*—Pithy.
- *Petiole length.*—The petiole ranges in length from 7 cm. to 16 cm.
- *Petiole diameter.*—The diameter of the petiole is 0.30 cm.
- *Leaf dimensions.*—21 cm. in length and 17 cm. in width.
- *Number of leaflets* (*per leaf*).—Leaflets range in number from 3–7 leaflets per leaf.
- *Leaflet shape.*—Ovate in shape.
- *Leaflet margins.*—Serrate.
- *Leaflet apex.*—Acute.
- *Leaflet base.*—Cuneate.
- *Leaflet surfaces* (*adaxial and abaxial surface*).—Glabrous.
- *Leaflet appearance* (*adaxial and abaxial surfaces*).—Semi-glossy.
- *Vein pattern.*—Pinnate.
- *Vein color* (*abaxial surface*).—187A.
- *Vein color* (*adaxial surface*).—191C.
- *Leaflet attachment.*—Petiolulate.
- *Petiolule surface.*—Glabrous.
- *Petiolule dimensions.*—6 mm. in length and 3 mm. in diameter.
- *Petiolule color.*—187A.
- *Petiolule shape.*—Sulcate.
- *Leaflet dimensions.*—Leaflet dimensions range from 7–10 cm. in length and 3.5–6.5 cm. in width on an individual leaf.
- *Leaflet color* (*adaxial surface*).—Individual colors 189A and 191C are both present on an individual leaflet.
- *Leaflet color* (*abaxial surface*).—Individual colors 191A and 187A are both present on an individual leaflet.
- *Stipules.*—None.
- *Foliar fragrance.*—None observed.

Flower:
- *Blooming season.*—Winter and spring.
- *Self-cleaning or persistent.*—Persistent sepals and self-cleaning nectaries.
- *Inflorescence type.*—Spicate.
- *Color of peduncle.*—182B.
- *Internode length.*—6 cm. in length.
- *Peduncle shape.*—Elliptic in cross-section.
- *Peduncle length.*—11 cm. in length.
- *Peduncle width.*—4 mm. in width.
- *Peduncle surface.*—Glabrous.
- *Pedicel color.*—166A.
- *Pedicel length.*—Length of pedicels on an individual peduncle can include a range of 2.5–6 cm. in length.
- *Pedicel diameter.*—2 mm. in diameter.
- *Pedicel surface.*—Glabrous.
- *Diameter of flower.*—5.50 cm. in diameter, increasing to 7.5 cm. as the flower ages.

*Depth of flower.*—1.50 cm. in depth.
*Flower shape.*—Obtusely stellate.
*Color of flowers* (*adaxial and abaxial surfaces*).—Individual colors 158C, 182B and 148D are all present on each individual flower over the course of the blooming period.
*Aspect.*—Slightly nodding.
*Petals.*—Present only as nectaries.
*Sepals.*—Five sepals in number.
*Sepal shape.*—Between ovate and orbicular.
*Sepal apex.*—Rounded.
*Sepal base.*—Rounded.
*Sepal surface* (*adaxial surface*).—Slightly puberulent.
*Sepal surface* (*abaxial surface*).—Slightly puberulent.
*Sepal margin.*—Entire.
*Sepal color* (*abaxial surface*).—Individual colors 158C, 182B and 148D are all present on an individual sepal over the course of the blooming period.
*Sepal color* (*adaxial color*).—Individual colors 158C, 182B and 148D are all present on an individual sepal over the course of the blooming period.
*Sepal length.*—2.5 cm. in length, increasing to 3.5 cm. as the flower ages.
*Sepal width.*—2 cm. in width, increasing to 2.5 cm. as the flower ages.
*Unfused or fused.*—Tepals are unfused.
*Bud color.*—158D, 148D, and 182B are individually present on an individual bud.
*Bud shape.*—Nux-shaped.
*Bud dimensions.*—1.75 cm. in length and 1.25 cm. in width.
*Bracts* (*subtending one bud*).—Two in number.
*Bract shape.*—Oval.
*Bract attachment.*—Sessile.
*Bract color* (*adaxial surface*).—138A.
*Bract color* (*abaxial surface*).—Colors 138B and 182B are individually present.
*Bract dimensions.*—1.25 cm. in width and 2.50 cm. in length.
*Bract margins.*—Mostly entire with a few small teeth.
*Bract apex.*—Acute.
*Bract base.*—Rounded.
*Bract surface.*—Glabrous.
*Quantity of flowers.*—Twelve flowers per spike.
*Lastingness of flower.*—An individual flower will last 10 days on the plant and 5–8 days off the plant, but will retain its shape for two months.
*Fragrance.*—None observed.

Reproduction organs:
*Stamens.*—Number of stamens range from 25–50.
*Color of stamens.*—149D.
*Dimensions of stamen.*—1 cm. in length and 0.50 mm. in width.
*Dimensions of anther.*—1.5 mm. in width and 2 mm. in length.
*Pollen color.*—154D.
*Amount of pollen.*—Moderate amount.
*Anther color.*—154D.
*Anther shape.*—Disc with longitudinal groove.
*Pistils.*—Five in number.
*Pistil dimensions.*—1.50 cm. in length and 7 mm. in width.
*Pistil shape.*—Group of 5 pistils is fountain-shaped ending in 5 slender tips.
*Pistil color.*—145C.
*Stigma dimensions.*—0.6 mm. in length and 0.7 mm. in width.
*Stigma color.*—Colors 155A and 148D are individually present.
*Nectary.*—13 in number.
*Nectary color.*—N144A.
*Nectary arrangement.*—Whorl.
*Nectary shape.*—Tubular.
*Nectary dimensions.*—7 mm. in length and 2.5 mm. in width.
*Ovary position.*—Superior.
*Ovary shape.*—Oval.
*Ovary dimensions.*—4 mm. in width and 7 mm. in length.
*Ovary color.*—145D.

Seed: Seed development has not been observed.

It is claimed:

1. A new and distinct variety of *Helleborus* plant named 'Walhelivor' as described, and illustrated.

* * * * *